United States Patent
Roberts et al.

(10) Patent No.: US 7,656,510 B2
(45) Date of Patent: Feb. 2, 2010

(54) STREAM-WISE THERMAL GRADIENT CLOUD CONDENSATION NUCLEI CHAMBER

(75) Inventors: Gregory C. Roberts, San Diego, CA (US); Athanasios Nenes, Mableton, GA (US)

(73) Assignees: The Regents of the University of California, Oakland, CA (US); California Institute of Technology, Pasadena, CA (US)

( * ) Notice: Subject to any disclaimer, the term of this patent is extended or adjusted under 35 U.S.C. 154(b) by 177 days.

(21) Appl. No.: 10/528,348

(22) PCT Filed: Sep. 18, 2003

(86) PCT No.: PCT/US03/29213

§ 371 (c)(1),
(2), (4) Date: Nov. 7, 2005

(87) PCT Pub. No.: WO2004/027380

PCT Pub. Date: Apr. 1, 2004

(65) Prior Publication Data

US 2006/0126056 A1    Jun. 15, 2006

Related U.S. Application Data

(60) Provisional application No. 60/411,688, filed on Sep. 18, 2002.

(51) Int. Cl.
  *G01N 1/00* (2006.01)
(52) U.S. Cl. ........................................ 356/37

(58) Field of Classification Search ................... 356/37; 73/28.01; 250/222.2
See application file for complete search history.

(56) References Cited

U.S. PATENT DOCUMENTS

| | | | | |
|---|---|---|---|---|
| 5,239,356 | A * | 8/1993 | Hollander et al. | 356/37 |
| 5,675,405 | A * | 10/1997 | Schildmeyer et al. | 356/37 |
| 5,922,976 | A | 7/1999 | Russell et al. | |
| 6,003,389 | A * | 12/1999 | Flagan et al. | 73/865.5 |
| 6,330,060 | B1 | 12/2001 | Flagan et al. | |
| 6,529,272 | B2 | 3/2003 | Flagan et al. | |
| 6,712,881 | B2 | 3/2004 | Hering et al. | |
| 6,809,314 | B2 * | 10/2004 | Yoshida et al. | 250/288 |
| 6,980,284 | B2 * | 12/2005 | Ahn et al. | 356/37 |

FOREIGN PATENT DOCUMENTS

WO    WO 2004/027380    4/2004

OTHER PUBLICATIONS

Albritton DL, Meiro Filho LG, "Technical summary," In: Climate Change 2001: The Scientific Basis. Contribution of Working Group I to the Third Assessment Report of the Intergovernmental Panel on Climate Change (Houghton JT, Ding Y, Griggs DJ, Noguer M, van der Linden PJ, Dai X, et al., eds). New York: Cambridge University Press, pp. 21-85.

(Continued)

*Primary Examiner*—Tarifur Chowdhury
*Assistant Examiner*—Tara S Pajoohi
(74) *Attorney, Agent, or Firm*—Fish & Richardson P.C.

(57) ABSTRACT

A cloud condensation nuclei instrument including an aerosol flow line (320) to carry a desired sample to the CNN chamber (310) and a temperature control unit (313A, 313B) to provide a monotonically increasing temperature profile along the direction of flow.

46 Claims, 6 Drawing Sheets

OTHER PUBLICATIONS

Bartlett, B. M., and G. P. Ayers, "Static diffusion cloud chamber," J. Rech. Atmos., vol. 15, No. 3-4: 231-233 (1981).

Charlson, R. J. et al., "Climate Forcing by Anthropogenic Aerosols," Science 255:423-430 (Jan. 24, 1992).

Chuang, P.Y., "Design of a CCN instrument for airborne measurement," Journal of Atmospheric and Oceanic Technology, 17: 1005-1019 (2000).

Chuang, P.Y. et al., "Kinetic limitations on droplet formation in clouds," Nature 390: 594-596 (Dec. 11, 1997).

Delene, D. J., "A balloon-borne cloud condensation nuclei counter," J. Geophys. Res., vol. 103, No. D8, pp. 8927-8934, (Apr. 27, 1998).

Facchini, M. C. et al., "Surface tension of atmospheric wet aerosol and cloud/fog droplets in relation to their organic carbon content and chemical composition," Atmospheric Environment 34: 4853-4857 (2000).

Fukuta, N., and V. Saxena, "A horizontal thermal gradient cloud condensation nucleus spectrometer," Journal of Applied Meterology, 18: 1352-1362, (Oct. 1979).

Hegg, D. A. et al., "Laboratory studies of the efficiency of selected organic aerosols as CCN," Atmospheric Research 58: 155-166 (2001).

Hoppel, W.A. et al., "A Segmented Thermal Diffusion Chamber for Continuous Measurements of the CN," Journal of Aerosol Science 10(4): 369-373 (1979).

Hudson, J. G., "An instantaneous CCN spectrometer," Journal of Atmospheric and Oceanic Technology, 6: 1055-1065 (1989).

Kaufman, Y.J. et al., "Smoke, Clouds, and Radiation—Brazil (SCAR-B) experiment," J. Geophys. Res. vol. 103, No. D24: 31783-31808 (1998).

Köhler, H. "The nucleus in and the growth of hygroscopic droplets," Trans. Faraday Soc., 32, 1152-1161 (1936).

Laaksonen, A.P. et al., "Modification of the Köhler equation to include soluble trace gases and slightly soluble substances," J. Atmos. Sci. 55: 853-862 (1998).

Lala, G. G., and J. E. Jiusto, "An automatic light scattering CCN counter," J. Appl. Meteor., 16: 413-418 (Apr. 1977).

Mircea, M. et al., "The influence of the organic aerosol component on CCN supersaturation spectra for different aerosol types," Tellus 54B: 74-81 (2002).

Nenes, A. et al., "A theoretical analysis of cloud condensation nucleus (CCN) instruments," J. Geophys. Res., 106: 3449-3474 (2001).

de Oliveira, J.C.P. and G. Vali, "Calibration of a photoelectric cloud condensation nucleus chamber," Atmospheric Research, 38: 237-248 (1995).

Raes, F., "The $2^{nd}$ Aerosol Characterization Experiment (ACE-2): general overview and main results," Tellus 52B: 111-125 (2000).

Ramanathan, V. et al., "Indian Ocean Experiment: An integrated analysis of the climate forcing and effects of the great Indo-Asian haze," J. Geophys. Res. vol. 106, No. D22, pp. 28371-28398 (Nov. 27, 2001).

Ramanathan, V. et al., "Aerosols, climate and the hydrological cycle," Science, 294(5549): 2119-2124 (2001).

Roberts, G.C. et al. "Sensitivity of CCN spectra on chemical and physical properties of aerosol," J. Geophys. Res., vol. 107, No. D20, 8070, 37-1 to 37-18, (2002).

Roberts, G.C. and A. Nenes, "A Continuous-Flow Streamwise Thermal-Gradient CCN Chamber for Atmospheric Measurements," Aerosol Science and Technology 39: 206-221 (2005).

Roberts, G.C. et al., "A Continuous-Flow Longitudinal Thermal-Gradient CCN Chamber for Airborne Measurements," Abstract for American Association for Aerosol Research, $21^{st}$ Annual AAAR Conference, Oct. 7-11, 2002, Charlotte, North Carolina, 1 page.

Rogers, C.F., and P. Squires, "A new device for studies of cloud condensation nuclei active at low supersaturations," Atmospheric Aerosols and Nuclei, Proceedings of the Ninth International Conference on Atmospheric Aerosols, Condensation and Ice Nueclei, edited by A. Roddy, and T. O'Connor, Galway University Press, University College, Galway, Ireland, Sep. 21-27, 1977, pp. 96-100.

Rosenfeld, D., "TRMM observed first direct evidence of smoke from forest fires inhibiting rainfall," Geophys. Res. Lett., vol. 26, No. 20, pp. 3105-3108, (Oct. 15, 1999).

Saxena, V. K., and J.C. Carstens, "On the operation of cylindrical thermal diffusion cloud chambers," Le Journal de Recherhes Atmosphériques, 5: 11-23 (1971).

Shulman, M.L. et al., "Dissolution behavior and surface tension effects of organic compounds in nucleating cloud droplets," Geophysical Research Letters vol. 23, No. 3, pp. 277-280 (1996).

Sinnarwalla, A. M. and D.J. Alofs, "A cloud nucleus counter with long available growth time," J. Appl. Meteor., 12: 831-835 (Aug. 1973).

Smolík, J. and V. Ždímal, "Condensation of Supersaturated Vapors of Dioctylphthalate: Homogeneous Nucleation Rate Meausurements," Aerosol Science and Technology 20(1): 127-134 (1994).

Twomey, S., "Measurements of natural cloud nuclei," Le Journal de Recherhes Atmosphériques, 1: 101-105 (1963).

Twomey, S., "The influence of pollution on the short-wave albedo of clouds," J. Atmos. Sci., 34: 1149-1152 (1977).

Twomey, S. and T.A. Wojciechowski, "Comments on 'Anomalous Cloud Lines,'" J. Atmos. Sci. 25: 333-334 (1969).

* cited by examiner

| ID # | Description |
|---|---|
| 410 | CCN column – location of temperature gradient between 413A and 413B |
| 412 | Wetted surface |
| 413A | Top temperature control |
| 413B | Bottom temperature control |
| 420 | Collection cone |
| 422 | Aerosol flow inlet |
| 424 | Sheath flow inlet |
| 430 | Mesh screen – flow straightener |

STREAM-WISE THERMAL GRADIENT CLOUD CONDENSATION NUCLEI CHAMBER

This application is a PCT national stage application of PCT/US03/29213, filed on Sep. 18, 2003. This application claims the benefit of U.S. Provisional Application No. 60/411,688 entitled "MEASUREMENT OF CLOUD CONDENSATION NUCLEI USING LONGITUDINAL THERMAL-GRADIENT CHAMBER" and filed on Sep. 18, 2002 by Gregory C. Roberts.

The research and development for inventions described in this application received funding under NSF Grant No. ATM94-05024 from the National Science Foundation. The U.S. Government may have rights to various technical features described in this application.

BACKGROUND

This application relates to aerosol measurements, and more particularly, to measurements of cloud condensation nuclei.

The effect of human activities on climate is being recognized as one of the most important issues facing society (International Panel of Climate Change, 2001). Humans influence climate in numerous ways by cooling or heating the planet. Some components (such as greenhouse gas warming) are well understood and quantified; others are subject to high uncertainty. Aerosols (airborne particulate matter) belong to the latter category. It is believed that aerosols have a net cooling effect, but quantitative estimates are highly uncertain, of the order of the greenhouse warming effect itself. This uncertainty primarily originates from poorly understood aerosol-cloud interactions. Aerosols are the seeds for cloud formation, and those, around which droplets form, are called cloud condensation nuclei (CCN). The size, concentration, and affinity to water vapor of CCN can directly influence the size and concentration of cloud droplets.

Increasing the concentrations of aerosols (which occurs under polluted conditions) leads to more reflective and persistent clouds. Since clouds are very effective reflectors of incoming solar radiation, even small perturbations in their properties can significantly decrease the amount of solar radiation absorbed by the climate system, and thus lead to cooling, otherwise known as the aerosol "indirect effect". Of all the components of climate change, the aerosol indirect effect is the most uncertain and potentially with the largest cooling effect. Until the aerosol indirect effect is well quantified, society is incapable of assessing its impact on future climate.

Measurements of CCN are fundamental for providing the link between cloud microphysics and the physical and chemical properties of aerosol. It is this liaison that is essential to improving our understanding of aerosol-cloud interactions and their subsequent effect on climate through modification of cloud radiative properties and the hydrological cycle. CCN measurements, however, are among the most challenging measurements in atmospheric sciences as obstacles in instrumental development and nuances in interpreting the data pose inherent problems. The primary source of problems lies in clouds themselves; they form in regions of very low water vapor supersaturation (by most a few tenths of a percent). Developing a technique that generates low supersaturation in a controlled manner, within in an ultralight package that responds quickly to ambient changes (necessary conditions for in-situ aircraft measurements), has proven to be challenging.

In addition, instrument development in this field has been largely empirical. As a result, measurements were often subject to unquantified uncertainty. Significant improvements in the measurement techniques are needed and this development constitutes an important step in this direction.

The ability of a particle to nucleate is at least in part determined by the saturation level of the environment, the size of the particle, and the chemical composition of the particle. When the relative humidity exceeds the saturation level where the vapor phase and the liquid phase are in equilibrium, a supersaturation state establishes and vapor begins to condense on surfaces and some particles. At a certain critical supersaturation, when the diameter of a condensation nucleus of a given chemical composition exceeds a critical diameter, the nucleus is said to be "activated." Upon this activation, vapor can condense spontaneously on that nucleus and cause the nucleus to grow to a very large size which is limited only by the kinetics of condensational growth and the amount of vapor available for the condensational growth. The critical diameter at a given supersaturation usually changes with the chemical composition of the particles. Hence, particles of different chemical compositions can become activated at different sizes. One way to characterize condensation nuclei is to measure the critical supersaturation at which a particle activates. Various cloud condensation nucleus spectrometers have been developed for producing and measuring supersaturations in a desired range.

It is generally understood that cloud formation is determined by a subset of aerosol particles that grow into droplets by heterogeneous water nucleation. The ability of an aerosol particle to serve as CCN depends primarily on its size and soluble mass. The ratio of water vapor pressure at the surface of the droplet to that of a flat plane is the equilibrium saturation ratio $S_R^{eq}$, and is described by the Köhler theory initially published by Köhler, "The nucleus in and the growth of hygroscopic droplets," Trans. Faraday Sot., 32, 1152-1161 (1936). See also, e.g., Pruppacher and Klett, Microphysics of Clouds and Precipitation, Kluwer Academic Publishers, Boston, (1997) and Seinfeld and Pandis, Atmospheric chemistry and physics: From air pollution to climate change, 1326 pp., John Wiley, New York (1998). Two competing terms describe the Köhler equation; the surface tension term (i.e., the Kelvin effect) accounts for enhanced vapor pressure due to droplet curvature and scales to inverse diameter, $D_p^{-1}$, and the dissolved solute term (i.e., the Raoult effect) depresses the water vapor pressure at the droplet surface and scales to $D_p^{-3}$. The maximum $S_R^{eq}$ of the Köhler curve defines the critical supersaturation, $S_c$, and occurs at the droplet's critical diameter, $D_{pc}$. The droplet is in stable equilibrium with its environment when its diameter is less than $D_{pc}$. However, once the particle has activated (i.e., $D_p > D_{pc}$), the particle will continue to grow as long as the surrounding vapor pressure of water in the air is greater than the equilibrium vapor pressure of the solution droplet. The saturation ratios are often expressed as supersaturations, $S_v$, in percent (i.e., $S_v (\%) = (S_R - 1) \times 100\%$).

The shape of the Köhler curve dictates droplet growth and can be readily modified by surfactants and slightly soluble constituents in ambient aerosols. The presence of surface-active substances, such as water-soluble organic carbons (WSOC), can have a significant influence on the equilibrium vapor pressure by reducing the droplet's surface tension, which lowers $S_c$ and enhances droplet growth. Slightly soluble compounds and soluble gases also affect the shape of the Köhler curve and may even allow the occurrence of stable, unactivated droplets of about 20 μm diameter in realistic, albeit polluted, conditions. Such modifications to the Köhler curve result in different growth rates of droplets and may impose challenges in defining activated and unactivated droplets and what constitutes CCN. Nonetheless, interpreting measurements from CCN instruments requires an understanding of these nuances and proper assessment of their importance in light of the particular experiment's focus.

SUMMARY

This application includes, among others, exemplary implementations of continuous-flow CCN chambers with improved measurement accuracy based on a monotonic thermal gradient in the stream-wise direction of the air flow. Such CCN chambers can be used for real-time, in-situ measurements of CCN and may be configured to operate at a high sampling rate sufficient for airborne operations. Direct measurements in the climatically important range of supersaturations of less than 0.1% are possible with the present CCN chambers.

The exemplary continuous-flow CCN chambers described here have a monotonic thermal gradient in the stream-wise direction of the air flow in the CCN chambers. Hence, the temperature of the CCN chamber changes monotonically along the flow direction from the input end to the output end. In general, the temperature may monotonically increase along the flow direction. In one implementation, for example, the temperature within the CCN chamber may linearly increase from the input end to the output end of the CCN chamber along the steam-wise direction. In a cylindrical CNN chamber, such a linear spatial temperature gradient can produce a quasi-uniform supersaturation along the flow direction. This quasi-uniform supersaturation along the flow direction can maximize the growth rate of activated droplets in the flow and thus significantly enhance the instrument performance. The temperature gradient and the flow control the supersaturation in the CCN chamber and may be adjusted or modified to retrieve the CCN spectra.

In one implementation, a CCN device includes a cloud condensation nuclei chamber having an input to receive an aerosol flow, a region of supersaturation to grow cloud condensation nuclei, and an output to export the aerosol flow. A thermal control is engaged to the chamber to produce a monotonic thermal profile in a stream-wise direction of the aerosol flow from the input to the output in the chamber.

In another implementation, a cloud condensation nuclei measuring apparatus has a chamber to receive an air sample and to keep the air sample in a region of supersaturation within a specified range, a heating system providing an increasing temperature gradient along the axis of the chamber in the direction of flow, and a particle counter coupled to the chamber to measure particles in the air sample output by the chamber and to provide a count indicative of particles within a selected size range.

In a more specific implementation, a CCN instrument is provided in which an air sample is introduced in the center of a vertical, cylindrical column whose surfaces are wetted. This configuration keeps the sample in a region of nearly uniform supersaturation and minimizes wall losses. The air then flows vertically downwardly through the chamber, where CCNs activate and grow into droplets. An optical particle counter at the outlet of the chamber detects all particles having diameters over a threshold such as 0.5 microns. Particles above a next threshold, for example, 1.0 microns are considered CCNs, and their total per unit volume comprises the CCN concentration. A monotonically increasing temperature gradient is provided along the axis of the chamber in the direction of flow.

These and other implementations and associated methods are described in greater detail with reference to the drawings, the detailed description, and the claims.

DETAILED DESCRIPTION

Figure 1:
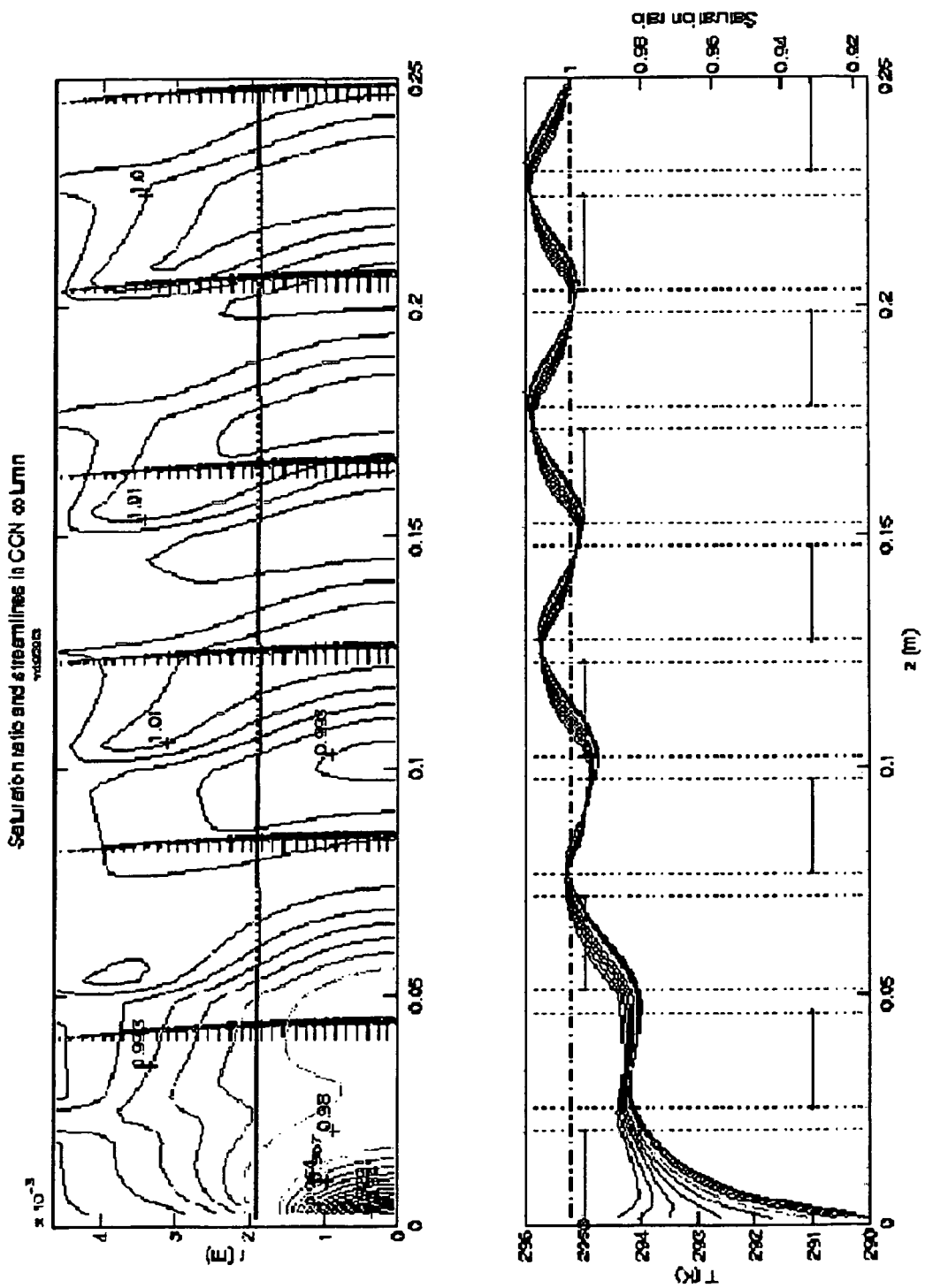
FIG. 1 shows computed saturation and thermal gradient in an alternating-gradient CCN chamber for repeating hot/cold sections in a cylindrical symmetry. The upper graph illustrates the contours of the supersaturation profile in the radial, r, and streamwise, z, dimensions. The centerline is at r=0. The lower graph shows the alternating temperature gradient (bars) and the development of the supersaturation profile near the centerline of the chamber (multiple oscillating lines). The dashed line denotes the transition between an undersaturated (ratio<1) and supersaturated (ratio>1) region of the instrument. Notice that the minimum supersaturation ratio briefly drops below 1 (<0% supersaturation) just after the cold sections. Droplets momentarily evaporate during this period.

The specific techniques and designs of continuous-flow CCN chambers with a monotonic thermal gradient in the stream-wise direction of the air flow are now described below as examples. These examples include implementations of continuous-flow CCN chambers employing a novel technique of generating a supersaturation along the streamwise axis of the chamber. Such a CCN instrument may establish a constant temperature gradient in the direction of flow to explore the differences in diffusion between water vapor and heat so that a quasi-uniform supersaturation at the centerline can be maintained. As described below, this quasi-uniform supersaturation is desirable in promoting continuous growth of the activated particles or droplets throughout the CCN instrument and thus improving reliability of the measurements.

The streamwise thermal-gradient CCN chambers described here can generate a well-defined supersaturation to simulate cloud-formation in a controlled environment. The some notable features of these CCN chambers include:

1. Temperature gradient in the streamwise direction generates the supersaturation by exploiting the difference in diffusion between heat and water vapor.

2. Continuous flow allows fast sampling (1 Hz measurements), which is suitable for airborne measurements.
3. Supersaturation is nearly constant at the centerline (for a constant and increasing temperature gradient), which maximizes droplet growth.
4. Supersaturation is a function of the flow rate, the pressure and the temperature profile inside the chamber, which can be easily controlled and maintained.
5. Simple cylindrical geometry reduces size and minimizes buoyancy (or other secondary flow) effects.

The principle of the CCN chambers has been validated by controlled laboratory experiments and independent measurements.

In a more specific implementation, such a CCN chamber may have a cylindrical column. The surfaces of the cylindrical column are wetted and exposed to an increasing and constant temperature gradient along the stream-wise axis constitutes the chamber volume. An air sample is introduced at the center of the column and is surrounded by an aerosol-free humidified sheath flow. This configuration keeps the sample in a region of nearly uniform supersaturation and minimizes wall losses. The air then flows through the chamber, where CCN activate and grow into droplets. An optical particle counter at the outlet detects and sizes all particles. Those particles larger than a threshold size (e.g., 1 micron diameter) are considered CCN. This design maximizes the growth rate of activated droplets, thereby enhancing the performance of the instrument. The temperature gradient and the flow through the column control the supersaturation and may be modified to retrieve the CCN spectra.

The underlying mechanism of generating a supersaturation relies on the difference in heat and mass diffusion as water vapor diffuses faster than heat (i.e., $0.25\ m^2\ s^{-1}$ vs. $0.21\ m^2\ s^{-1}$ at 294 K, 1 atm, respectively). The resulting supersaturation is largely dependent on the temperature gradient and flow rate; while changes in pressure and temperature affect rates of diffusion and exert a secondary effect.

The exemplary continuous-flow CCN chambers described here have a continuous thermal gradient in the stream-wise direction of the air flow in the CCN chambers. For example, the thermal gradient may be a monotonic thermal gradient in the stream-wise direction of the air flow in the CCN chambers. Hence, the temperature of the CCN chamber changes monotonically along the flow direction from the input end to the output end. The temperature may monotonically increase along the flow direction. In one implementation, the temperature of the cylindrical CCN chamber increases linearly along the flow direction from the input end to the output end. A linear temperature gradient yields a quasi-uniform supersaturation along the centerline and maximizes the growth rate of activated droplets, thereby significantly enhancing the instrument performance. This monotonic streamwise temperature gradient not only improves the performance of the CCN instrument but also makes the design simpler.

Figure 3:
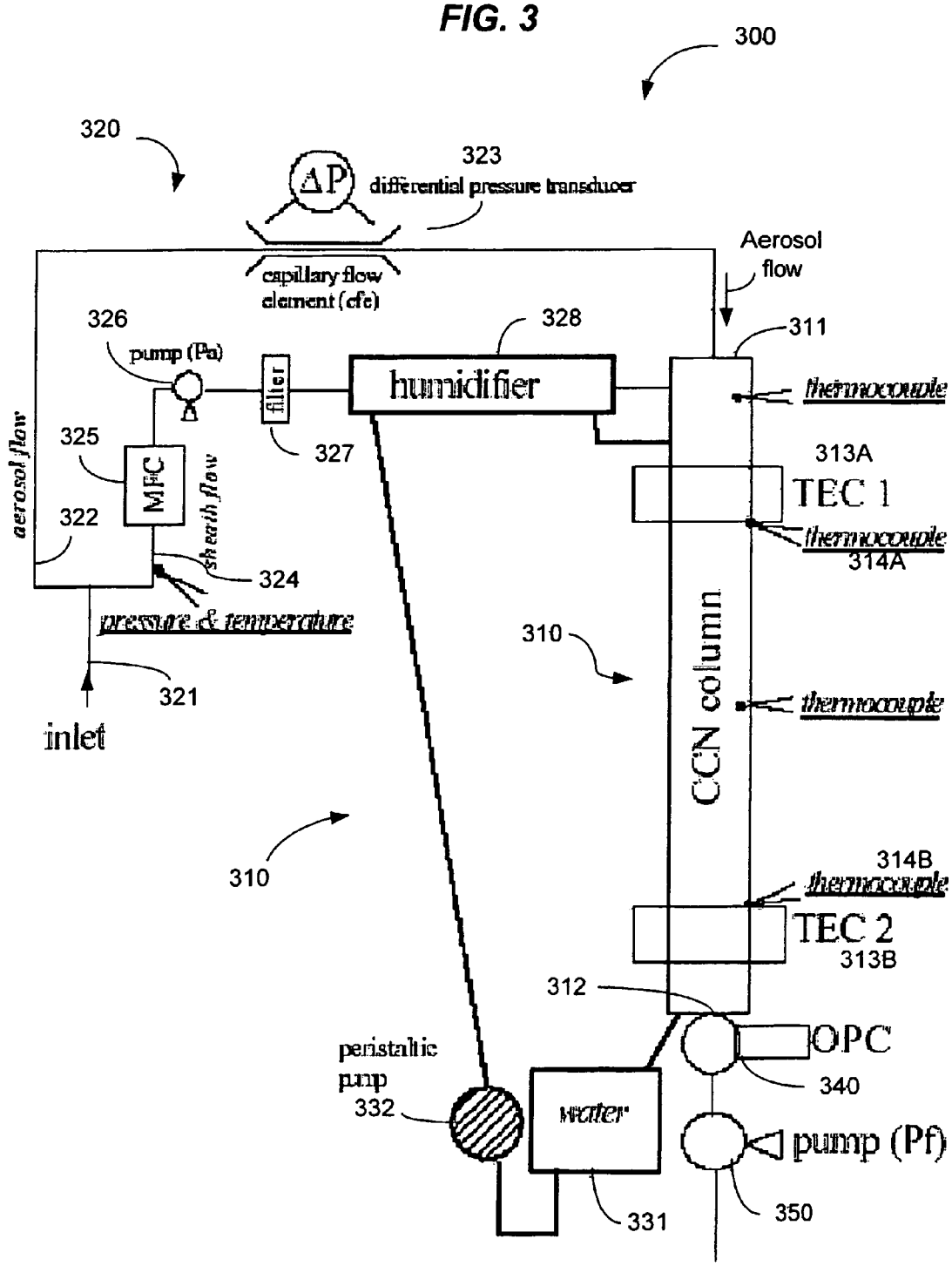
FIG. 3 shows one example of a CCN chamber described in this application.

FIG. 3 shows one exemplary implementation of a CCN instrument 300 having a continuous-flow CCN chamber 310 with a monotonic thermal gradient in the stream-wise direction of the air flow. The system 300 includes an aerosol flow line 320 to carry a desired sample flow to the chamber 310 received from the Y-shaped inlet 321. The inlet 321 splits the input air flow into an aerosol flow in an aerosol flow pathway 322 and a sheath flow in a sheath flow pathway 324. A mass flow controller 325 and a pump 326 are located in the sheath flow pathway 324 to produce the desired volumetric sheath flow to the chamber 310. A total particle filter 327 is also in the sheath flow line 324 to remove all particles in the sheath flow. A volumetric flow element 323, e.g., a capillary flow element coupled with a differential pressure transducer, may be placed in the aerosol flow pathway 322 to measure the volumetric flow rate of the aerosol flow which will be fed into the entrance section 311 to undergo the condensation in the chamber 310.

A water supply module 330 is also included in the system 300 to circulate water through the chamber 310 to humidify the sheath flow and to wet the inner wall of the chamber. A water reservoir 331 is provided to supply water to the top of the chamber 310 and to uptake excess water from the bottom of the chamber 310. A water pump 332 may be used to supply the water from the reservoir 331 to a humidifier 328 in the sheath flow line 324 to humidify the sheath flow and supply the water to the top of the chamber 310.

At the outlet of the chamber 310, a particle counter 340 collects output air flow to measure the number of droplets (e.g., activated particles) in the aerosol flow. This particle counter 340 may be an optical particle counter (OPC) or other suitable counters to measure droplet size and concentration. An air pump 350 may be coupled in the output flow to induce the aerosol flow in the chamber 310 and to further control the flow rate.

The design in FIG. 3 has distinct features in comparison with other CCN chambers. For example, U.S. Pat. No. 6,330,060 to Flagan and Chuang describes a CCN chamber with alternating hot and cold temperature-control sections to produce a spatially alternating thermal gradient along the flow direction. The supersaturation profile in this alternating gradient CCN chamber is oscillating along the axis of the chamber in the direction of the flow. Hence, the residence time a particle is exposed to a given supersaturation limits or even reverses growth of activated droplets.

FIG. 1 shows the alternating-gradient technique for repeating hot/cold sections in cylindrical symmetry. The upper graph illustrates the contours of the supersaturation profile in the radial, r, and streamwise, z, dimensions. The centerline is at r=0. The arrows show the parabolic velocity profile. The lower graph shows the alternating temperature gradient (bars) and the development of the supersaturation profile near the centerline of the chamber (multiple oscillating lines). The minimum saturation ratio briefly drops below 1 (i.e., subsaturated) just after the cold sections. Droplets momentarily evaporate during this period. Simulations of the alternating-gradient technique achieved only marginal performance using a fully-coupled model developed by Nenes, Chuang, Flagan, and Seinfeld in "A theoretical analysis of cloud condensation nucleus (CCN) instruments," J. Geophys. Res., 106, 3449-3474 (2001).

In recognition of the above, the inventors conducted simulations on the alternating-gradient design and adjusted various instrument parameters to improve the performance. In a particular simulation, successive sections were heated slightly warmer than previous ones to prevent the airstream from equilibrating in a single heated section (i.e., the diffusion time of water vapor and heat to the center of the cylindrical chamber was longer than the residence time of the air parcel in a given heated section). This pattern was extended along the column and produced a nearly constant centerline supersaturation with small oscillations about the mean value. Smaller simulated heated sections and a more uniform increase in temperature resulted in a linear temperature gradient and a smooth, nearly uniform centerline supersaturation.

Figure 2:
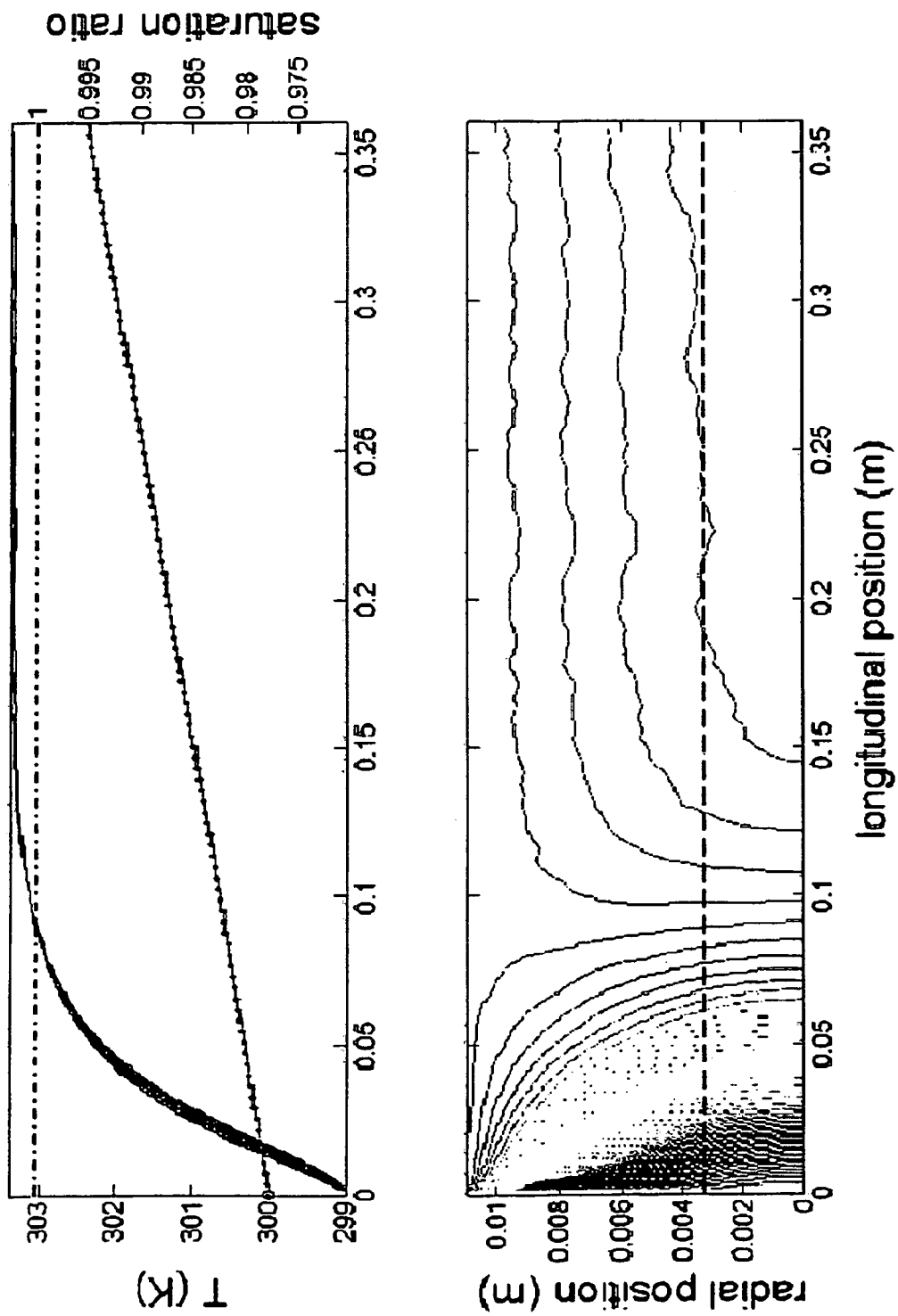
FIG. 2 shows saturation and thermal profiles of a linear thermal-gradient CCN chamber in a cylindrical symmetry. The upper graph illustrates the contours of the supersaturation profile in the radial and streamwise dimensions. The centerline is at r=0. The lower graph shows the linear temperature gradient (line with dot symbol) and the development of the uniform supersaturation profile near the centerline of the chamber. Notice that unlike FIG. 1, the supersaturation is always positive (or ratio>1) throughout most of the instrument.

FIG. 2 shows two plots of the simulation results based on the linear thermal-gradient technique for a cylindrical symmetry. The upper graph illustrates the contours of the supersaturation profile in the radial and streamwise dimensions.

The centerline is at r=0. The lower graph shows the linear temperature gradient (lines with dot symbols) and the development of the uniform supersaturation profile near the centerline of the chamber.

The design in FIG. 3 implements this linear thermal-gradient technique. Instead of controlling each of the multiple sections (i.e., 14 hot/cold sections) as in U.S. Pat. No. 6,330,060, a continuous temperature gradient can be established by maintaining the temperature at a minimum of two locations 313A and 313B—at each end of the chamber 310. Other features and associated advantages of this design are described below.

In FIG. 3, the CCN chamber 310 is an elongated, cylindrical chamber having an entrance section 311 to receive an input air flow along the longitudinal direction of the chamber and an output section 312 to export the air flow for measurements of CCN. The chamber 310 may be oriented vertically with the entrance section 311 on the top and the output section 312 at the bottom. Thermal control units may be thermally coupled to the ends of the chamber 310 to maintain a thermal gradient in the chamber 310 along the flow direction. The thermal gradient establishes a monotonic change in temperature along the wetted surface in the flow direction, e.g., an increase in the wall temperature from the entrance section 311 to the output section 312. As illustrated, each temperature control unit 313A and 313B may include one or more thermal control devices that are spatially separated along the chamber 310. For example, one or more thermal electric coolers (TECs) may be used to produce the desired stream-wise monotonic thermal gradient in the chamber 310. Temperature sensors, such as thermocouples 314A and 314B, may be used to monitor the temperature at different locations within the chamber 310.

The system 300 in FIG. 3 provides a much needed improvement to the measurements of CCN by providing a simple, yet, robust method of precisely generating a supersaturation in a cylinder. More detailed features of the system 300 are now provided in the following sections.

Temperature Control

In the illustrated example, a vertical cylindrical column is used as the CCN growth chamber 310. The column's inner surfaces are wetted and exposed to an increasing temperature gradient along the streamwise, vertical axis. The dimensions of the column may be about 10.9 mm in radius. The length and wall thickness depend on the operating conditions and may be about 360 mm in length with a wall thickness of about 8 mm. To generate a nearly-linear temperature gradient, the column's walls should be sufficiently thick such that heat transfer in the streamwise axis (within the wall) is much greater than the convective or evaporative heat losses to the sample aerosol flow and through the insulation surrounding the column. Four thermal electric coolers (TECs) may surround the column on each end to maintain the prescribed temperatures at their respective locations and maintain a desired monotonic temperature gradient along the axis of the chamber. The TECs may be mounted on each side of a 34 mm×34 mm×38 mm block which securely fits around the column. Heat-conductive silicon paste may be applied between the TECs, block and the column to ensure proper heat transfer. Temperature measurements may be made at several locations shown in FIG. 3. Thermocouples, resistance temperature detectors (RTDs), and other temperature sensors may be used.

The top column temperature 314A operates near the temperature surrounding the instrument. The sheath flow that flows against the inner wall of the column 310 may be actively heated in the headblock 311 with, e.g., a resistance wire heater, to slightly above top column temperature (ca. 1 K) to prevent inadvertent activation of particles in the entrance portion of the column where the sample and sheath flows rejoin. Another resistance wire heater may be used to keep the optical particle counter 340 (OPC) slightly warmer than the bottom-column temperature 314B to prevent condensation of water vapor on the optics and detector in the OPC.

Flow Control

An example of the CCN instrument 300 flow system is also shown in FIG. 3. A Y-shaped inlet 321 splits the sample airstream into separate aerosol and sheath flows while minimizing impaction losses. The aerosol sample flows through a capillary and a differential pressure sensor (e.g., 5" $H_2O$ full-scale, temperature compensated Honeywell sensor) may measure the volumetric flow. Electrically conductive silicon tubing for the aerosol flow line 324 is made as short as possible to minimize diffusion losses.

Figure 4:
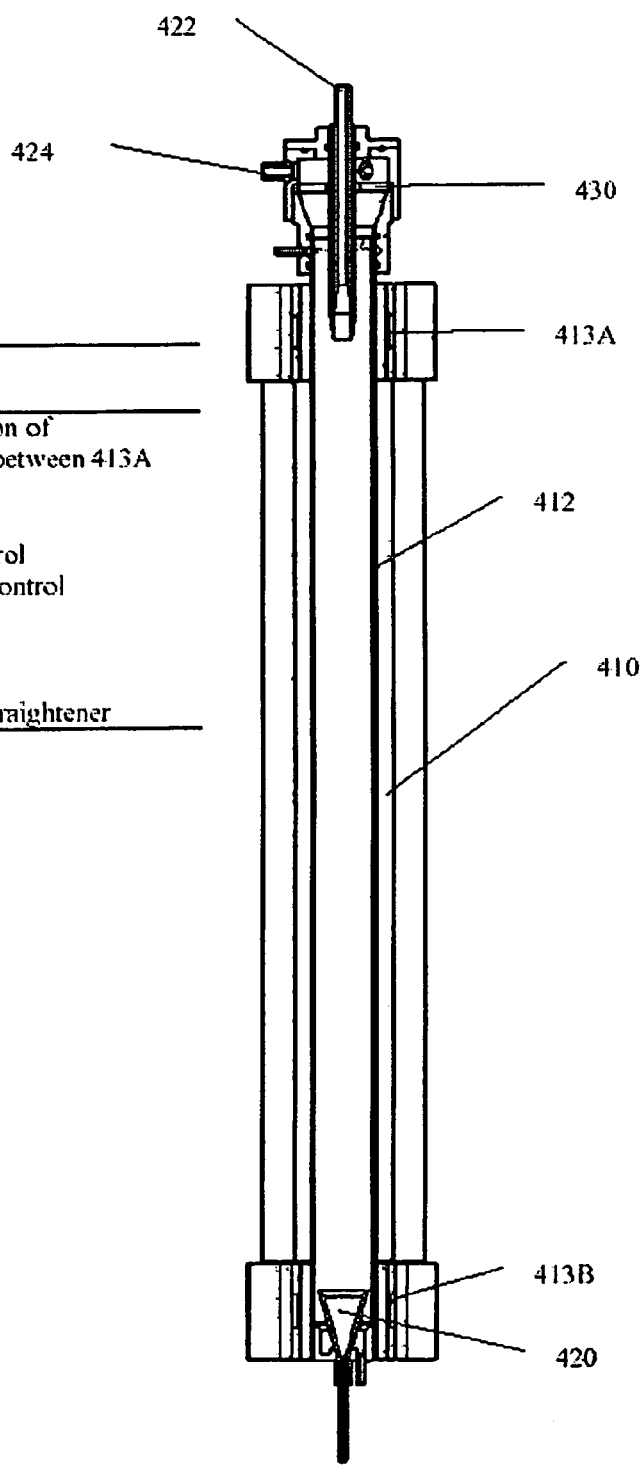
FIG. 4 shows the internal structure that enables annular flow through the column that is used in the exemplary CCN chamber in FIG. 3.

The sheath flow is directed through a total aerosol filter 327, flow meter 325, pump 326, orifice, dead-volume, humidifier and heater before being introduced into the headspace above the wetted column. A mesh 430, shown in FIG. 4, separates the headspace and the wetted column, and via a slight pressure gradient uniformly distributes the aerosol-free humidified sheath flow. Before rejoining with the aerosol flow, the sheath flow is accelerated into the growth column; once it has achieved fully developed, annular flow, the air sample is introduced at the center of the wetted column. This annular configuration keeps the aerosol flow in a region of nearly uniform supersaturation and confines the aerosol flow near the centerline to minimize wall losses. The measurements nominally used a 10-to-1 volumetric ratio for the sheath and aerosol flow rates which are also referred to as a sheath-to-aerosol ratio (SAR) of 10. Configurations with SARs between 5 and 20 have been tested.

After the sheath and aerosol flows have been rejoined, the air then flows vertically downward through the chamber (FIG. 4) and is exposed to the increasing temperature gradient along the wetted surface within the chamber. Particles with a critical supersaturation less than the centerline saturation ratio activate and grow into droplets. The length of the column and flow rate may be optimized to achieve sufficiently large particles to separate activated and unactivated droplets. A collector cone 420 at the bottom of the chamber may focus the sample at the bottom of the chamber and introduces the airstream into the OPC. The cone 420 may have an included angle of 30° (i.e., 15° from the flow axis), and its opening may be slightly smaller than the chamber diameter so that excess water drains along the walls without flooding the OPC 340. A pump 350 downstream of the OPC 340 pulls the airstream through the instrument 300. Dead-volumes and orifices may be placed between each of the pumps and the column to eliminate pressure oscillations in the growth chamber.

Optical Particle Counter

The optical particle counter (OPC) 340 in the system 300 in FIG. 3 may employ standard light scattering techniques to detect droplets at the outlet of the growth column. The OPC is available commercially through, e.g., MetOne Intruments, Inc. (Grants Pass, Oreg., USA). The electronics processor from MetOne counts and sizes the detector output into six size-selectable bins, which may be selected to be 0.5, 0.7, 1.0, 2.0, 3.0, 6.0 μm diameter. The size cutoffs of the bins have been calibrated at MetOne and the smallest detectable particle size is 0.3 μm diameter. The number count of particles with diameters greater than the bin size may be exported via a RS-232 communication interface at 1 Hz.

A collection cone may be attached to the OPC to bring the sample into the scattering volume with minimal bias to the droplet size spectra. Those droplets larger than a threshold (e.g., 1.0 μm diameter) may be considered CCN and comprise the CCN concentration.

Column Wetting

Various materials may be used on the inner surface of the chamber 310 in FIG. 3 to provide the desired wetting. For example, two layers of filter paper 412 (Whatman 1) may be used to maintain a wetted inner surface of the chamber. A reservoir 331 below the column may supply the water to a pump 332 (e.g. peristaltic pump), which pushes the water through a humidifier 328 (e.g., from Perma-Pur Inc.) and into the top of the column. Water is introduced through a radial band of small holes at top of the column for uniform distribution around the filter paper. Excess water drains to the bottom of the column and back into the reservoir. A gun-barrel-type drill on the inner side of the conductive wall 410, under the wetted surface 412, may result in a more efficient wetting of the walls, as well as a more efficient way to drain excess liquid water from the walls.

Electronics Interface

The electronic interface for the CCN instrument 300 in FIG. 3 may be designed for automatic acquisition and control of various operations. Its main parts may include a microprocessor or microcontroller such as an industry standard x86 compatible NEC V25 microcontroller, an interface backplane and various extension boards, which interface the process controller to the various components. Because of its high modularity, the system may be easily scaleable and, therefore, adaptable to the development of the CCN instrument. The interface is assembled in a standard 19" rack-mounted container. Seven analog-to-digital (A/D) input channels (16 bit resolution, low noise, 50 Hz suppression) collect temperature and differential pressure measurements. Eight digital-to-analog (D/A) channels (12 bit, low noise, 50 Hz suppression) control the thermal electric coolers, pumps, and resistance heaters. Data storage capabilities on PCMCIA hard disks provide ample storage space, and an RS-232 interface is also available to connect to secondary hosts. An integrated menu-driven LCD and 6 keyboard user interface provide an efficient, user-friendly interface for controlling various parameters and assessing the performance of the instrument.

Design of Instrument

Flow and streamline constraints on the instrument in FIG. 3 are now described. Before constructing the instrument, extensive simulations using the fully coupled model of various parameters (i.e., column dimensions, heating rates, and flow rates) placed operational and dimensional constraints on the instrument design. In particular, special attention was devoted to buoyancy-related issues that affect the instrument's performance. Earlier attempts to produce a similar instrument failed because of degraded performance resulting, in part, from secondary (buoyancy) flows that developed using large temperature gradients and low flow rates. Parameters such as column radius, temperature, temperature gradient and flow rate must be carefully selected to ensure proper performance.

Figure 6:
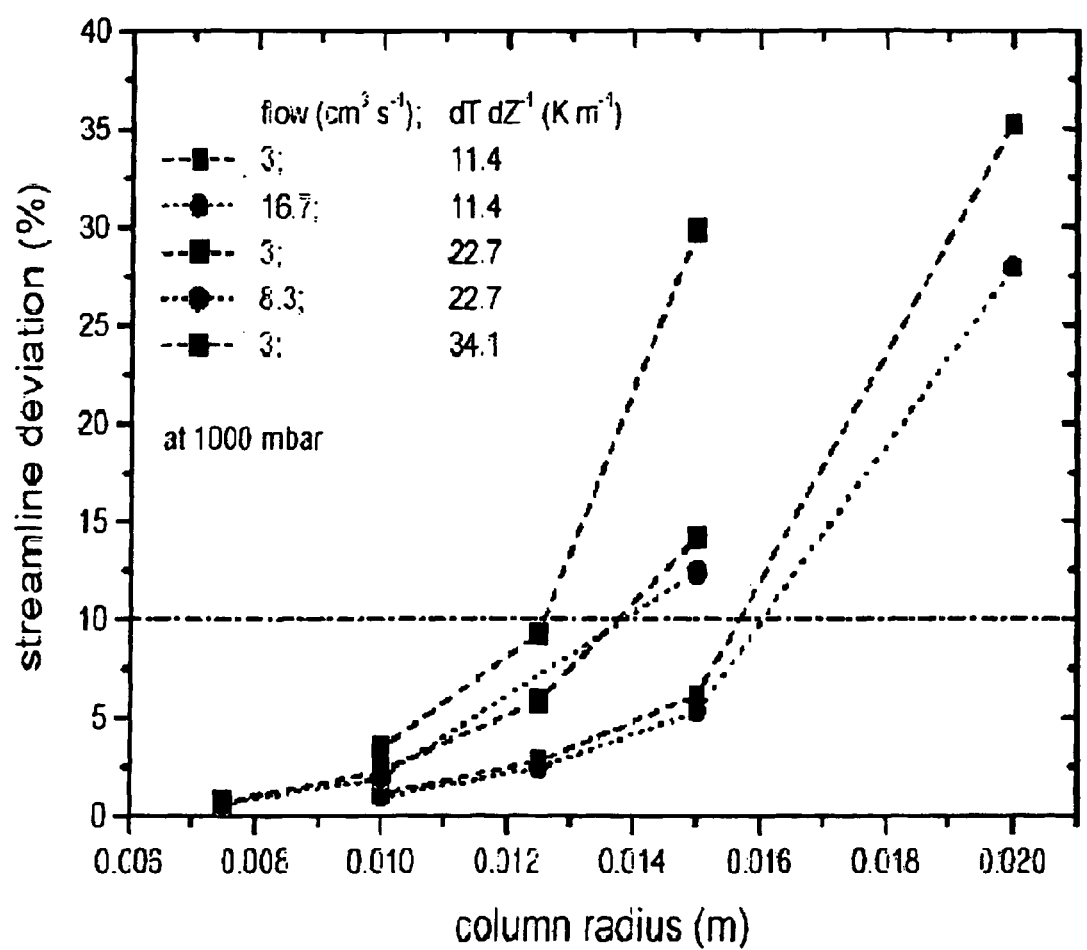
FIG. 6 shows simulations of streamline deviations in the chamber as a function of column radius for a range of flow rates and temperature gradients.

One important dimension of the instrument is the column radius, which dictates the droplet's residence time in the column (hence, allowable growth). Instrument performance was measured by determining the ratio of the maximum radial change in the streamlines (maximum amount of change in streamlines perpendicular to the flow) to the radius of the column. Simulations were performed by using the fully coupled model that cover the operating range of the CCN instrument as shown in FIG. 6. For all simulated conditions, even at low flows and large temperature gradients, there is a notable increase in the deviation of streamlines as the radius increases above 12 mm.

In addition, buoyancy effects may also set limits on the maximum temperature gradients. As one might expect, large temperature gradients also drive unwanted convective motion as shown by the onset of convective activity at smaller radii in FIG. 6; and ultimately, limiting the maximum supersaturation at a given flow rate. Simulations indicate that the maximum supersaturation for the current configuration is ca. 3% at 1 liter per minute, which is sufficiently high for ambient measurements.

At small supersaturations, low flow rates may be needed to provide the residence time required for adequate growth for detection or distinguishing the activated droplets from deliquesced particles. However, low flow rates are more susceptible to buoyancy effects and are ultimately limited by the terminal settling velocity of growing droplets. We operate the CCN instrument with flow in the downward vertical direction to eliminate problems associated with the suspension of larger droplets in the sample flow. The above-described instrument based on FIG. 3 was tested to be operable for flow rates between 0.3 and 1 lpm.

The instrument in FIG. 3 may be capable of producing supersaturations less than 0.1%. In this operating range, it is important to distinguish activated droplets from deliquesced particles for identifying CCN according to the Köhler curve definition. As discussion earlier, a particle is consider activated when the droplet grows beyond its critical diameter, $D_{pc}$; where it will continue to grow as long as there is sufficient water vapor. This growth process, however, is diffusion limited and a finite time is required to grow the droplets. Distinguishing activated from unactivated droplets is relatively straightforward for small aerosol particles whose critical diameters are significantly less than the 1 μm threshold. However, as particles become larger, the critical size approaches the detection size and activated and unactivated droplets are not readily identified. To obtain measurements of CCN at lower supersaturations, we need to increase the threshold to larger sizes; however, there is a trade-off between this threshold and the residence time needed for adequate growth.

An analytical solution of maintaining a constant supersaturation in a cylindrical column is described below for an ideal fully developed, laminar flow. This solution determines the supersaturation at any point within the chamber. The generalized conservation principle for steady-state laminar flow in axisymmetric coordinates can be expressed as $$u\frac{\partial X}{\partial z} + v\frac{\partial X}{\partial r} = \frac{\alpha}{r}\frac{\partial}{\partial r}\left(r\frac{\partial X}{\partial r}\right) \qquad (1)$$

where X is either temperature or water vapor; u and v are stream velocities in the streamwise, z, and radial, r, directions, and α is the thermal or water vapor diffusivity in air. The terms on the left-hand side account for fluid motion; and those on the right-hand side account for diffusion. The solution to the above equation is readily obtained for fully developed flow at steady state with no convection, no slip boundary, and constant surface heat flux. The equation reduces to $$X(r) = X_s - \frac{2u_m r_o^2}{\alpha}\left(\frac{dX}{dz}\right)\left[\frac{3}{16} + \frac{1}{16}\left(\frac{r}{r_o}\right) - \frac{1}{4}\left(\frac{r}{r_o}\right)^2\right] \quad (2)$$

where $X_s$ is the surface temperature or water vapor pressure, $u_m$ is the mean flow velocity through the tube, and $r_o$ is the radius of the column. Obtaining the value of the temperature profile, dT/dz, is trivial in the implementation of a linear thermal gradient along the z axis. However, the equilibrium vapor pressure, C, increases with temperature and the expression for dC/dz is shown to be $$\frac{dC}{dz} = \gamma_1 \cdot \exp\left[\frac{\gamma_1 \cdot (T-T_o)}{(T-\gamma_2)}\right] \cdot \frac{dT}{dz} \cdot \left(\frac{\gamma_1 \cdot (T-T_o)}{(T-\gamma_2)}\right)^2 \quad (3)$$

where $T_o$ is 273.15 K, and $\gamma_1$, $\gamma_2$ and $\gamma_3$ are constants (6.113× $10^{-3}$, 17.67 and 26.95, respectively). The saturation (%), which decreases slightly along the z axis, is defined as $$S = \left(\frac{C}{C_{eq}} - 1\right) \cdot 100\% \quad (4)$$

where $C_{eq}$ is the equilibrium water vapor pressure at a given temperature within the column.

The validity of this simplified analytical approximation has been verified through model comparisons and laboratory experiments. A comparison of the simplified model and the fully coupled model suggests that the main features of the dual diffusion in laminar flow in a cylindrical tube have been captured. The main differences between the two models arise from transient non-laminar flows and convective motions. The longer hydrodynamic entry length at larger flows impedes the development of a parabolic laminar profile causing the deviations in supersaturation predictions with respect to the flow rate. Differences in the diffusivities and density from changes in temperature are also not considered in the simplified analysis.

Figure 5:
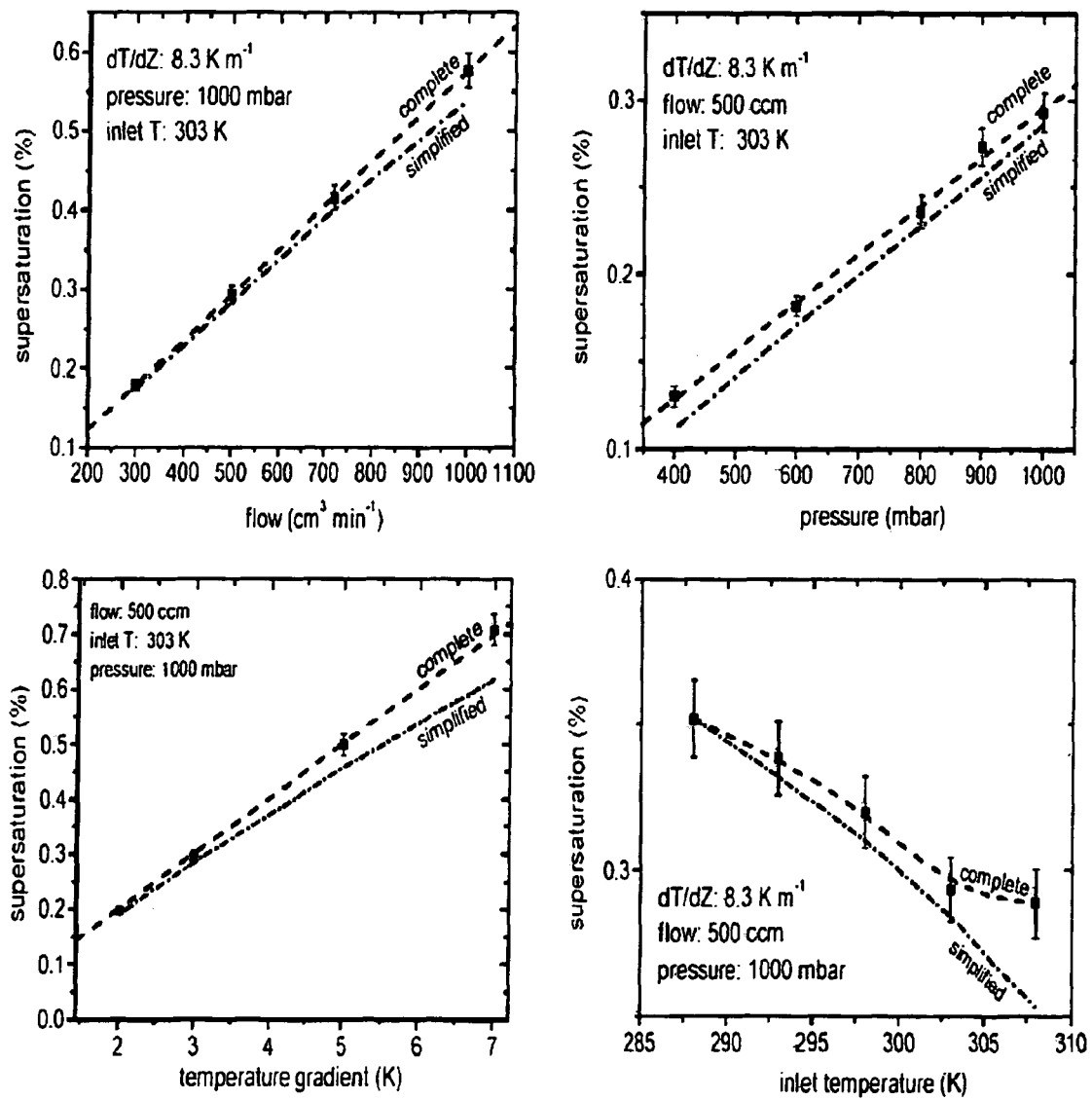
FIG. 5 shows predictions of supersaturation based on simplified and fully-coupled model simulations for individual variables at conditions similar to normal operation. The error bars on the fully-coupled simulations represent one-sigma variations to the mean centerline supersaturation.

The analytical steady-state and fully-coupled transient model simulations present the characteristics of the CCN instrument and illustrate the dependence of the supersaturation at various operating conditions. FIG. 5 illustrates this dependence on several important variables, including flow, temperature gradient, pressure and temperature. The flow rate and temperature gradient exert the largest influence on determining the supersaturation; where the rate of change in supersaturation is ca. 0.06% per 100 cm³ min⁻¹ change in flow rate and 0.10% per K m⁻¹ change in temperature gradient. The absolute pressure and entrance temperature of the column also influence the supersaturation by changing the rate of diffusion; however, the effects of absolute pressure and temperature are modest at ca. 0.03% per 100 mbar and 0.034% per 10 K, respectively. Nonetheless, slight changes in $S_v$ are expected during vertical profiles in airborne measurements. A typical profile may cover a range between 600 and 700 mbar, which corresponds to a ca. 0.2% change in $S_v$. To maintain a constant $S_v$, one may vary other parameters such as the temperature gradient or flow rate to compensate the pressure dependence in $S_v$.

Additional modifications to the current design include but are not limited to the following:

1. Capillary flow elements simplify measurements of volumetric flow rates compared to mass flow meters, because they eliminate the need for pressure and temperature compensation during flight missions. The differential pressure sensors also require less power than mass flow controllers.
2. The wall thickness of the chamber needs to be minimized, yet sufficiently thick such that heat conduction in the longitudinal direction is greater than convective and evaporative losses from the sides.
3. Maintaining a wet column has been a challenge for CCN instruments. Currently, the Whatman filter paper is used to line the inside of the chamber. Other materials may also be used for maintaining desired wet surfaces in the column. For example, porous ceramics, such as alumina bisque, may also serve as the wetting medium. The thermal conductivity of alumina bisque ceramics (4.3 W K⁻¹ m⁻¹) is much higher than that of paper (0.18 W K⁻¹ m⁻¹), leading to smaller temperature differences between measured and wetted-surface temperatures. The use of ceramics also reduces the need of accessing the internal parts of the instruments making it more robust and "field-friendly."
4. Since the supersaturation exhibits a flow-rate and pressure dependence, feedback on the temperature and/or flow control must compensate for changes in pressure during vertical profiles to maintain a fixed supersaturation.

In addition, other implementations may be possible. For example, the temperature profile may increase or decrease along the streamwise axis and need not be linear. A non-linear temperature profile may apply to certain applications.

Also, the temperature profile may not necessarily be monotonic along the entire length of the column. For example, additional temperature control may be added such that the first part of the column may experience an increasing temperature gradient, whereas the latter part of the column may experience a decreasing or no temperature gradient.

The instrument may comprise at least two or more CCN columns with different particle counters to perform simultaneous measurements in parallel on air samples taken at the same locale. These columns may be at different lengths, or may be exposed to different operating conditions such as temperature gradients, internal pressures, different flow rates, and/or different media.

The CCN chamber designs here may apply to media other than the typical the medium of air and water and in general may apply to measurements in any media that exhibit different rates of mass and thermal diffusivity. The construction of the instrument and column may include materials other than aluminum and the walls of the chamber may consist of materials other than filter paper. Detectors or other devices other than an optical particle counter may also be used depending on the application. Air flow pattern in the CCN chamber other than annular flow through the column may also be acceptable. Furthermore, the instrument need not necessarily be positioned in the vertical direction.

What is claimed is:
1. A device, comprising:
   a cloud condensation nuclei chamber having an input to receive an aerosol flow, a region of supersaturation to grow cloud condensation nuclei, and an output to export the aerosol flow, said cloud condensation nuclei chamber being oriented vertically to receive the aerosol flow from said input at the top and export the aerosol flow from said output at the bottom to direct the aerosol flow in a downward direction along a direction of the gravity; and a thermal control engaged to said chamber to produce both a monotonic thermal profile and a monotonic temperature gradient in a stream-wise direction of the aerosol flow from said input to said output in said cloud condensation nuclei chamber.

2. The device as in claim 1, wherein a temperature in said cloud condensation nuclei chamber monotonically increases along the aerosol flow.

3. The device as in claim 2, wherein the temperature of said cloud condensation nuclei chamber linearly increases along the aerosol flow.

4. The device as in claim 2, wherein the temperature of said cloud condensation nuclei chamber nonlinearly increases along the aerosol flow.

5. The device as in claim 1, further comprising a flow control mechanism to split an air sample flow into the aerosol flow and a sheath flow, wherein the sheath flow is directed to flow along inner surfaces of said cloud condensation nuclei chamber to keep the aerosol flow away from the inner surfaces.

6. The device as in claim 5, wherein the sheath flow has a sheath flow rate higher than a flow rate of the aerosol flow.

7. The device as in claim 5, comprising:
a humidifier in a path of the sheath flow to provide a controlled humidity in the sheath flow; and
a mechanism to supply a liquid to wet an inner wall of the cloud condensation nuclei chamber.

8. The device as in claim 1, wherein said cloud condensation nuclei chamber has a cylindrical shape to direct the aerosol flow along an axis of the cylinder.

9. The device as in claim 1, wherein the temperature gradient in the cloud condensation nuclei chamber monotonically decreases along the aerosol flow.

10. The device as in claim 9, wherein the temperature gradient of the cloud condensation nuclei chamber linearly decreases along the aerosol flow.

11. The device as in claim 9, wherein the temperature gradient of the cloud condensation nuclei chamber nonlinearly decreases along the aerosol flow.

12. The device as in claim 1, wherein the cloud condensation nuclei chamber has a chamber wall with a selected chamber wall thickness sufficiently large to make heat transfer in the chamber wall along the stream-wise direction greater than heat losses to the aerosol flow and to surrounding of the chamber.

13. The device as in claim 1, wherein the cloud condensation nuclei chamber comprises an additional cloud condensation nuclei chamber segment that connects to the cloud condensation nuclei chamber and has a thermal profile different from the monotonic thermal gradient profile of the cloud condensation nuclei chamber.

14. The device as in claim 13, wherein the monotonic thermal gradient profile in said chamber has a linearly increasing thermal gradient and the thermal profile of said additional cloud condensation nuclei chamber segment has a linearly decreasing thermal gradient.

15. The device as in claim 13, wherein the thermal profile of said additional cloud condensation nuclei chamber segment has a constant temperature with a zero thermal gradient.

16. The device as in claim 1, wherein the aerosol flow includes a gas that is different from air.

17. The device as in claim 1, comprising a mechanism to supply a liquid to wet an inner wall of said the cloud condensation nuclei chamber.

18. The device as in claim 17, wherein the liquid is different from water.

19. The device as in claim 17, wherein the inner wall of the cloud condensation nuclei chamber, which is wetted by the liquid, is made from a porous ceramic material.

20. The device as in claim 17, wherein the inner wall of the cloud condensation nuclei chamber, which is wetted by the liquid, is made from alumina bisque.

21. The device as in claim 17, wherein the inner wall surface includes gun-barrel-type grooves to assist the wetting of the inner wall surface.

22. The device as in claim 1, comprising a feedback control that controls at least one of (1) a temperature of the cloud condensation nuclei chamber and (2) the aerosol flow to maintain a fixed supersaturation in the cloud condensation nuclei chamber.

23. The device as in claim 1, comprising a mechanism that modifies (1) the monotonic thermal gradient profile in the stream-wise direction of the aerosol flow and (2) the aerosol flow to generate cloud condensation nuclei spectra from the cloud condensation nuclei chamber.

24. The device as in claim 1, comprising a mechanism for controlling sizes of aerosol particles of the aerosol flow in the cloud condensation nuclei chamber to be counted to increase a size threshold for particle counting at a low supersaturation and to decrease the size threshold at a high supersaturation.

25. The device as in claim 1, wherein the monotonic temperature gradient linearly increases in the stream-wise direction of the aerosol flow.

26. The device as in claim 1, wherein the monotonic temperature gradient nonlinearly increases in the stream-wise direction of the aerosol flow.

27. A cloud condensation nuclei measuring apparatus, comprising:
a chamber to receive an air sample from a selected sampling location and to keep said air sample to flow in a downward direction along a direction of the gravity in a region of supersaturation within a specified range;
a heating system providing a linearly increasing temperature gradient along the axis of said chamber in the direction of flow; and
a particle counter coupled to said chamber to measure particles in said air sample output by said chamber and to provide a count indicative of particles within a selected size range, and
wherein the heating system is structured and controlled to produce both the linearly increasing temperature gradient along the axis of said chamber in the direction of flow and a monotonic thermal profile in a stream-wise direction of the flow and to effectuate a nearly constant supersaturation along said chamber.

28. The apparatus as in claim 27, further comprising a flow control mechanism to provide a sheath flow around the air sample in said chamber and to keep the air sample away from side walls of said chamber.

29. The apparatus as in claim 28, wherein a ratio of a flow rate of the sheath flow over a flow rate of the air sample is controlled between 5 and 20.

30. The apparatus as in claim 28, further comprising a heating element to heat the sheath flow at a temperature above a temperature of an end of the said chamber that receives the air sample.

31. The apparatus as in claim 27, wherein said chamber has a wetted inner surface.

32. The apparatus as in claim 31, wherein said chamber has a layer of a filter paper on the wetted inner surface.

33. The apparatus as in claim 31, wherein said chamber has a layer of a porous ceramic material on the wetted inner surface.

34. The apparatus as in claim 27, wherein said particle counter includes an optical particle counter.

35. The apparatus as in claim 27, further comprising:
a second chamber to receive a second air sample from the selected sampling location and to keep said second air sample in a region of supersaturation within a specified range;
a second heating system providing a second increasing temperature gradient along the axis of said second chamber in the direction of flow; and
a second particle counter to measure particles in said second air sample output from said second chamber and to provide a count indicative of particles within a second selected size range so that said first chamber and said second chamber operate in parallel to obtain two different aerosol measurements at the selected sampling location.

36. The apparatus as in claim 35, wherein said first chamber and said second chamber have different lengths.

37. The apparatus as in claim 35, wherein said first chamber and said second chamber have different temperature gradients.

38. The apparatus as in claim 35, wherein said first chamber and said second chamber have different flow rates.

39. The apparatus as in claim 35, wherein said first chamber and said second chamber have different internal pressures.

40. A thermal gradient diffusion chamber for inclusion in a cloud condensation nuclei measurement apparatus comprising a cloud condensation nuclei column that forms a hollow channel to direct a received aerosol flow; a flow control mechanism to split an air sample flow into the aerosol flow along a first path and a sheath flow along a second, different path and comprising a particle filter in the sheath flow to remove particles in the sheath flow, and a humidifier in the sheath flow to provide a controlled humidity in the sheath flow, the flow control mechanism coupled to the cloud condensation nuclei column to direct the sheath flow to flow along inner surfaces of the cloud condensation nuclei column to keep the aerosol flow away from the inner surfaces; a heat source to create an increasing temperature gradient and a monotonic thermal profile in the direction of flow of the aerosol flow in said chamber; and a particle counter coupled to the cloud condensation nuclei column to measure particles in said air sample output by the cloud condensation nuclei column and to provide a count indicative of particles within a selected size range.

41. The chamber in claim 40, wherein said chamber has a wetted inner surface.

42. The chamber as in claim 40, wherein the increasing temperature gradient along the axis of said chamber linearly increases.

43. A method for conditioning a sample in a cloud condensation nuclei measurement apparatus, comprising:
subjecting a sample passing through a column to form a sample flow; and
subjecting said sample to an increasing temperature gradient in the direction of the sample flow and to have a monotonic thermal profile in a stream-wise direction of the sample flow to produce a substantially constant supersaturation.

44. The method as in claim 43, further comprising using a sheath flow around the sample flow to keep the sample flow away from inner surfaces of the column.

45. The method as in claim 43, further comprising maintaining inner surfaces of the column wet with water.

46. A method comprising:
directing an aerosol flow through a cloud condensation nuclei chamber to grow particles due to condensation from supersaturation; and
controlling a temperature profile of the cloud condensation nuclei chamber along the aerosol flow to produce a nearly constant supersaturation along the cloud condensation nuclei chamber;
wherein a temperature of the cloud condensation nuclei chamber increases monotonically along the direction of the aerosol flow.

* * * * *

UNITED STATES PATENT AND TRADEMARK OFFICE
CERTIFICATE OF CORRECTION

PATENT NO. : 7,656,510 B2 Page 1 of 1
APPLICATION NO. : 10/528348
DATED : February 2, 2010
INVENTOR(S) : Gregory C. Roberts and Athanasios Nenes It is certified that error appears in the above-identified patent and that said Letters Patent is hereby corrected as shown below:

Column 1, lines 12-16, delete the following paragraph:
"The research and development for inventions described in this application received funding under NSF Grant No. ATM94-05024 from the National Science Foundation. The U.S. Government may have rights to various technical features described in this application."

and insert the following paragraph:

--FEDERALLY SPONSORED RESEARCH OR DEVELOPMENT
The invention was made with government support under Grant No. ATM94-05024 awarded by National Science Foundation. The government has certain rights in the invention.--;

IN THE CLAIMS:
Column 14, line 2 (Claim 17), after "wall of" delete "said";
Column 16, line 11 (Claim 41), after "The chamber" insert --as--.

Signed and Sealed this

Sixth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,656,510 B2 Page 1 of 1
APPLICATION NO. : 10/528348
DATED : February 2, 2010
INVENTOR(S) : Roberts et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 437 days.

Signed and Sealed this

Thirtieth Day of November, 2010

David J. Kappos
*Director of the United States Patent and Trademark Office*